United States Patent [19]
Giordano et al.

[11] Patent Number: 5,315,005
[45] Date of Patent: May 24, 1994

[54] PROCESS FOR THE SINGLE CRYSTALIZATION OF ENANTIOMERIC RATIO'S (2S,3S):(2R,3R) OF SUBSTITUTED 1,5-BENZOTHIAZEPINONE

[75] Inventors: Claudio Giordano, Monza; Dario Tentorio, Vigano'; Laura Russo, Milan, all of Italy

[73] Assignee: Zambon Group S.p.A., Vicenza, Italy

[21] Appl. No.: 8,892

[22] Filed: Jan. 25, 1993

Related U.S. Application Data

[63] Continuation of Ser. No. 547,045, Jul. 2, 1990, abandoned.

[30] Foreign Application Priority Data

Jul. 12, 1989 [IT] Italy .................. 21166 A/89

[51] Int. Cl.$^5$ ......................................... C07D 281/02
[52] U.S. Cl. ........................ 540/491; 540/488
[58] Field of Search .......................... 540/491

[56] References Cited

U.S. PATENT DOCUMENTS

| | | | |
|---|---|---|---|
| 3,562,257 | 2/1971 | Kugita et al. | 260/239.3 |
| 4,416,819 | 11/1983 | Nagao et al. | 540/500 |
| 4,420,628 | 12/1983 | Inoue et al. | 560/17 |
| 4,533,748 | 8/1985 | Manghisi et al. | 562/401 |

FOREIGN PATENT DOCUMENTS

| | | |
|---|---|---|
| 0325965 | 8/1989 | European Pat. Off. . |
| 53-018038 | 6/1978 | Japan . |

OTHER PUBLICATIONS

March, J. Advance Organic Chemistry, John Wiley and Sons, New York, 1985, pp. 104–107.
Hiroatsu et al; Chemical Abstract vol 90, 1979, 90: 6431w.
Biserka et al; Chemical Abstract vol. 101, 1984, 101: 109919m.
Merck Index, X Ed., No. 3189, p. 466, 1983.
The Pharmacopoeia of Japan, English Version, XI Edition (1986).
Chem. Abstract. 75:36164u (JP 71/8982-Tanabe Seiyaku Co., Ltd.), 1975.
Helvetica Chimica Acta, vol. 67, No. 3, 2 May 1984, pp. 916–926.
Organicum, pp. 38–39, 1973.
Encyclopedia of Chemical Technology, 3rd Edition, vol. 7, pp. 247, 260, 261, 1978.
Merck Index, X Ed., No. 3189, p. 466, 1983.

*Primary Examiner*—Mukund J. Shah
*Assistant Examiner*—Y. N. Gupta
*Attorney, Agent, or Firm*—Stevens, Davis, Miller & Mosher

[57] ABSTRACT

A purification method of intermediates for the preparation of Diltiazem which consists of the crystallization of a mixture enantiomerically enriched in (2S,3S)-2,3-dihydro-3-hydroxy-2-(4-methoxyphenyl)-1,5-benzothiazepin-4(5H)-one is described.

3 Claims, No Drawings

PROCESS FOR THE SINGLE CRYSTALIZATION OF ENANTIOMERIC RATIO'S (2S,3S):(2R,3R) OF SUBSTITUTED 1,5-BENZOTHIAZEPINONE

This application is a continuation of application Ser. No. 07/547,045, filed Jul. 2, 1990 now abandoned.

The present invention relates to a purification method of intermediate useful for the preparation of benzothiazepines and, more particularly, it relates to a purification method by crystallization of (2S,3S)-2,3-dihydro-3-hydroxy-2-(4-methoxyphenyl)-1,5-benzothiazepin-4(5H)-one of formula

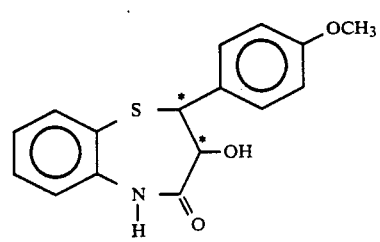

intermediate useful for the synthesis of Diltiazem.

Diltiazem, (+)-(2S,3S)-3-acetoxy-5-[2-(dimethylamino)ethyl]-2,3-dihydro-2-(4-methoxyphenyl)-1,5-benzothiazepin-4(5H)-one (Merck Index, X Ed., no. 3189, page 466), is a known drug with calcium-antagonist activity described in the British Pat. No. 1236467 (Tanabe Seiyaku Co. Ltd.).

Several methods of preparation of Diltiazem such as, for example, those described in the above cited British patent no. 1236467, in the European patent application no. 59335 (Tanabe Seiyaku Co. Ltd.) and in the Japanese patent no. 71/8982 (Tanabe Seiyaku Co. Ltd.) (C.A.: 75:36164u) are known in the literature.

Most of these methods substantially foresee the following synthesis scheme.

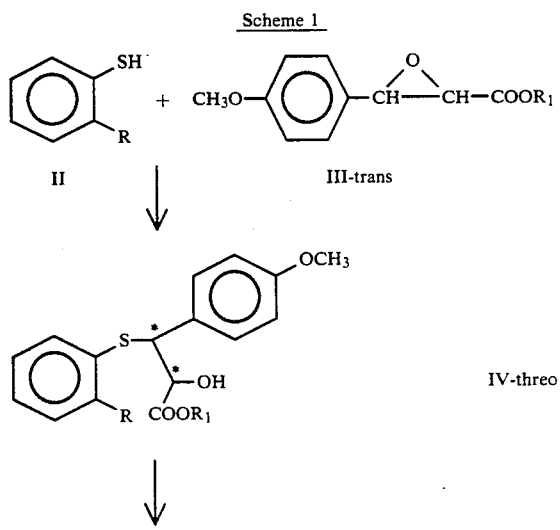

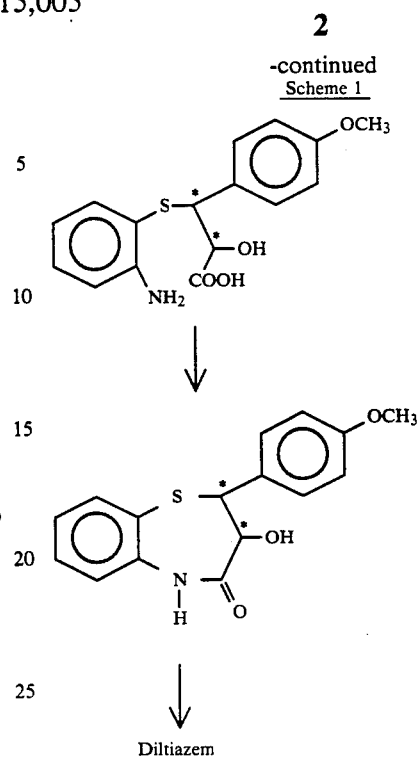

wherein R represents an amino or nitro group; $R_1$ represents a lower alkyl and the asterisks indicate the asymmetric carbon atoms.

Each of these methods necessarily comprise an optical resolution step, in general at the level of one of the intermediates of the synthesis, to separate the (2S,3S) enantiomer from the (2R,3R).

In fact, the resolution of the intermediate of formula V by optically active bases such as alpha-phenylethylamine, described in the European patent no. 98892 (Tanabe Seiyaku Co. Ltd.) and L-lysine, described in the British patent application no. 2130578 (Istituto Luso Farmaco d'Italia S.p.A.) is known.

It is important to underline that these resolutions when carried out did not provide the desired product in enantiomerically pure form but only as a mixture enantiomerically enriched in this product.

Accordingly it was necessary to carry out at least two resolutions in order to obtain the enantiomerically pure product.

It is clear to the man skilled in the art the advantage of carrying out, after the resolution of the racemic mixture, a purification, which affords an increase in the enantiomeric excess (e.e.), in order to obtain in a simple and economic way enantiomerically pure Diltiazem with the required physico-chemical characteristics [The Pharmacopoeia of Japan, English version, XI edition, (1986)] without the need of further purification or resolution.

We have now surprisingly found that, starting from a mixture enantiomerically enriched in (2S,3S) enantiomer of the intermediate of formula I, by a single crystallization the enantiomerically pure intermediate I is obtained in very good yield.

Accordingly it is object of the present invention a purification method of the (2S,3S)-2,3-dihydro-3- hydroxy-2-(4-methoxyphenyl)-1,5-benzothiazepin-4-(5H)-one of formula I which consists of the crystallization of a mixture enantiomerically enriched in the (2S,3S) enantiomer of the compound of formula I in an organic solvent selected among lower alcohols, aromatic hydrocarbons and ketones optionally in admixture with dipolar aprotic solvents.

Specific examples of organic solvents are lower alcohols such as methanol, ethanol, isopropanol and butanol, aromatic hydrocarbons such as xylene, toluene, chlorobenzene and o.dichlorobenzene or ketones such as acetone.

Specific examples of dipolar aprotic solvents are dimethylsulfoxide, dimethylformamide and sulfolane.

The amount of aprotic dipolar solvent optionally present in the mixture can vary between 10% and 40% by weight.

The filtration temperature of the crystallized product can vary, in general, between 0° C. and 65° C. depending on the solvent used but it is preferably comprised between 20° C. and 25° C.

It is important to underline that, by the purification process object of the present invention, the enantiomerically pure (2S,3S) enantiomer of formula I is obtained in very good yield, starting from mixtures with an enantiomeric ratio (2S,3S):(2R,3R) generally higher than 75:25 by carrying out one crystallization only.

As far as we know it does not exist any purification method of the intermediate I which does not comprise a new resolution, even starting from a mixture with an enantiomeric ratio of 90:10.

A practical embodiment of the invention, particularly useful in its industrial application, is the following.

The intermediate of formula V-threo, obtained for example by resolution according to one of the above reported methods, is cyclized in aromatic hydrocarbons such as xylene.

To the hot cyclization mixture a suitable amount of a dipolar aprotic solvent, e.g. dimethylformamide or dimethylsulfoxide is added.

The mixture is left to cool spontaneously up to room temperature optionally by seeding the crystallization by adding a small amount of enantiomerically pure compound of formula I.

The pure (2S,3S) enantiomer of formula I is thus obtained in very good yield, from this Diltiazem is then prepared by alkylation and acetylation according to known methods.

The process object of the present invention shows a very good industrial applicability allowing to purify mixtures enantiomerically enriched in (2S,3S) enantiomer of the intermediate of formula I by a simple crystallization with good yield and high productivity Moreover, as already underlined, the crystallization can be carried out by processing directly the cyclization reaction mixture without separating the intermediate I.

By the purification process of the present invention it is possible therefore to obtain Diltiazem with high purity without the need of further purification.

In order to better illustrate the present invention, the following examples are given.

EXAMPLE 1

In a flask equipped with a reflux condenser, a thermometer and a stirrer, a mixture of 2,3-dihydro-3-hydroxy-2-(4methoxyphenyl)-1,5-benzothiazepin-4(5H)-one in the ratio (2S,3S):(2R,3R)=90:10 (1 g; 3.3 mmols) and methanol (50 ml) was added.

The mixture was heated until complete dissolution.

The obtained solution was left to cool spontaneously to 20° C., optionally by seeding the crystallization by adding a small portion of optically pure (2S,3S)-2,3-dihydro-3-hydroxy-2-(4-methoxyphenyl)-1,5-benzothiazepin-4(5H)-one.

The precipitate was filtered, always at 20° C., washed with methanol and the product was dried in oven under vacuum at 65° C.

(2S,3S)-2,3-dihydro-3-hydroxy-2-(4-methoxyphenyl)-1,5-benzothiazepin-4(5H)-one (0.66 g) was obtained in 73% yield, calculated on the amount of (2S,3S) enantiomer present in the starting mixture. From polarimetic and NMR analysis the obtained product resulted to have an optical purity higher than 99%.

EXAMPLES 2–16

By working as described in example 1 the tests reported on the table were carried out.

TABLE

| Example | Solvent | Solvent Volume | (2S,3S):(2R,3R) ratio in the starting mixture | Filtration temperature | Yield | (2S,3S):(2R:3R) ratio in the crystallized |
|---|---|---|---|---|---|---|
| 2 | methanol | 20 ml | 90:10 | 24° C. | 89% | 95:5 |
| 3 | methanol/DMF | 20 ml (3 ml DMF) | 90:10 | 22° C. | 73% | 99:1 |
| 4 | methanol | 50 ml | 80:20 | 22° C. | 66% | 99:1 |
| 5 | ethanol | 50 ml | 90:10 | 24° C. | 80% | 99:1 |
| 6 | isopropanol | 65 ml | 90:10 | 23° C. | 86% | 99:1 |
| 7 | methanol/DMF | 10 ml (3.5 ml DMF) | 90:10 | 24° C. | 69% | 99:1 |
| 8 | methanol/DMF | 20 ml (4 ml DMF) | 80:20 | 22° C. | 62% | 100 |
| 9 | chlorobenzene | 25 ml | 90:10 | 23° C. | 90% | 98.5:1.5 |
| 10 | methanol | 50 ml | 90:10 | 0° C. | 83% | 95:5 |
| 11 | acetone | 25 ml | 90:10 | 24° C. | 51% | 100 |
| 12 | acetone | 25 ml | 90:10 | 14° C. | 59% | 100 |
| 13 | xylene/DMF | 7.6 ml (2 ml DMF) | 90:10 | 25° C. | 50% | 100 |
| 14 | methanol/DMF | 20 ml (3.7 ml DMF) | 80:20 | 24° C. | 52% | 100 |

TABLE-continued

| Example | Solvent | Solvent Volume | (2S,3S):(2R,3R) ratio in the starting mixture | Filtration temperature | Yield | (2S,3S):(2R:3R) ratio in the crystallized |
|---|---|---|---|---|---|---|
| 15 | methanol/sulfolane | 20 ml (4.9 ml sulfolane) | 80:20 | 25° C. | 41% | 100 |
| 16 | o.dichlorobenzene | 25 ml | 90:10 | 65° C. | 39% | 97:3 |

Notes to table:
DMF: dimethylformamide
DMSO: dimethylsulfoxide

EXAMPLE 17

In a reactor, equipped with in-jacket, reflux condenser, thermometer and stirrer, a mixture of methyl ester of threo-2-hydroxy-3-(2-aminophenylthio)-3-(4-methoxyphenyl)-propionic acid in the ratio (2S,3S):(2R,3R)=90:10 (5 g; 0.015 mols), paratoluensulfonic acid monohydrate (80 mg) and xylene (33.5 ml) was added.

The reaction mixture was reflux heated (about 138° C.) for 5 hours. While keeping the temperature higher than 135° C. dimethylformamide (2.3 ml) was added.

The mixture was left to cool spontaneously to room temperature, by seeding the crystallization at 110° C. with optically pure (2S, 3S)-2,3-dihydro-3-hydroxy-2-(4-methoxyphenyl)-1,5-benzothiazepin-4(5H)-one.

After filtration, the solid was washed with xylene (3 ml) and dried in oven under vacuum at 65° C.

The enantiomerically pure (2S,3S)-2,3-dihydro-3-hydroxy-2-(4-methoxy-phenyl)-1,5-benzothiazepin-4(5H)-one (3.59 g) was obtained in 88.2% yield calculated on the amount of (2S,3S) enantiomer present in the starting mixture.

What we claim is:

1. A purification process of (2S,3S)-2,3-dihydro-3-hydroxy-2-(4-methoxyphenyl)-1,5-benzothiazepin-4(5H)-one consisting of the single crystallization without conversion to diastereomers of a mixture enantiomerically enriched in the (2S,3S) enantiomer of 2,3-dihydro-3-hydroxy-2-(4-methoxyphenyl)1,5-benzothiazepin-4(5H)-one, such that the enantiomeric ratio (2S,3S):(2R,3R) is at least 75:25, in an organic solvent selected from the class consisting of lower alcohols, aromatic hydrocarbons and ketones optionally in admixture with dipolar aprotic solvents.

2. A process according to claim 1 wherein the organic solvent is selected from the class consisting of methanol, ethanol, isopropanol, butanol, xylene, toluene, chlorobenzene, o.dichlorobenzene and acetone.

3. A process according to claim 1 wherein the aprotic dipolar solvent is selected from the class consisting of dimethylsulfoxide, dimethylformamide and sulfolane.

* * * * *